United States Patent
McSweeney et al.

(10) Patent No.: US 11,712,424 B2
(45) Date of Patent: *Aug. 1, 2023

(54) NON-THERAPEUTIC METHODS FOR ALLEVIATING OR REDUCING STRESS SYMPTOMS OF RUMINANTS

(71) Applicant: DSM IP ASSETS B.V., Heerlen (NL)

(72) Inventors: Chris McSweeney, St Lucia (AU); Gonzalo Martinez Fernandez, St Lucia (AU); Stuart Edward Denman, St Lucia (AU); Horst Joachim Paul Peter Schirra, Brisbane (AU)

(73) Assignee: DSM IP ASSETS B.V., Heerlen (NL)

( * ) Notice: Subject to any disclaimer, the term of this patent is extended or adjusted under 35 U.S.C. 154(b) by 162 days.

This patent is subject to a terminal disclaimer.

(21) Appl. No.: 16/960,690

(22) PCT Filed: Jan. 23, 2019

(86) PCT No.: PCT/EP2019/051595
§ 371 (c)(1),
(2) Date: Jul. 8, 2020

(87) PCT Pub. No.: WO2019/145345
PCT Pub. Date: Aug. 1, 2019

(65) Prior Publication Data
US 2020/0352875 A1    Nov. 12, 2020

(30) Foreign Application Priority Data
Jan. 24, 2018 (EP) .................................... 18153285

(51) Int. Cl.
| | | |
|---|---|---|
| *A61K 31/04* | (2006.01) | |
| *A61P 43/00* | (2006.01) | |
| *A61K 31/02* | (2006.01) | |
| *A61K 47/02* | (2006.01) | |

(52) U.S. Cl.
CPC .............. *A61K 31/04* (2013.01); *A61K 31/02* (2013.01); *A61K 47/02* (2013.01); *A61P 43/00* (2018.01)

(58) Field of Classification Search
CPC ........ A61K 31/04; A61K 31/02; A61K 47/02; A61P 43/00
See application file for complete search history.

(56) References Cited

U.S. PATENT DOCUMENTS

2009/0022826 A1    1/2009    Shrier et al.

FOREIGN PATENT DOCUMENTS

| CN | 106540129 | 3/2017 |
|---|---|---|
| WO | 01/26482 | 4/2001 |
| WO | 2004/043898 | 5/2004 |
| WO | 2009/150264 | 12/2009 |
| WO | 2012/084629 | 6/2012 |

OTHER PUBLICATIONS

Matthew Butawan, et al., "Methylsulfonylmethane: Applications and Safety of a Novel Dietary Supplement", Nutrients, vol. 9, No. 3, Mar. 16, 2017, 21 pages.
Evert C. Duin, et al., "Mode of action uncovered for the specific reduction of methane emissions from ruminants by small molecule 3-nitrooxypropanol", Proceedings of the National Academy of Sciences of the United States of America, May 2, 2016, 6 pages.
G.W. Lanigan, "Metabolism of Pyrrolizidine Alkaloids in the Ovine Rumen. IV.* Effects of Chloral Hydrate and Halogenated Methanes On Rumen Methanogenesis and Alkaloid Metabolism in Fistulated Sheep", Australian Journal of Agricultural Research, vol. 23, No. 6, Jan. 1, 1972, 7 pages.
Gonzalo Martinez-Fernandez, et al., "3-NOP vs. Halogenated Compound: Methane Production, Ruminal Fermentation and Microbial Community Response in Forage Fed Cattle", Frontiers in Microbiology, vol. 9, Aug. 7, 2018, 14 pages.
International Search Report for PCT/EP2019/051595 dated Apr. 17, 2019, 5 pages.
Written Opinion of the ISA for PCT/EP2019/051595 dated Apr. 17, 2019, 7 pages.

*Primary Examiner* — Snigdha Maewall
(74) *Attorney, Agent, or Firm* — Nixon & Vanderhye P.C.

(57) ABSTRACT

The present invention relates to the reduction of stress in ruminants in need thereof.

13 Claims, No Drawings

NON-THERAPEUTIC METHODS FOR ALLEVIATING OR REDUCING STRESS SYMPTOMS OF RUMINANTS

This application is the U.S. national phase of International Application No. PCT/EP2019/051595 filed Jan. 23, 2019 which designated the U.S. and claims priority to EP Patent Application No. 18153285.4 filed Jan. 24, 2018, the entire contents of each of which are hereby incorporated by reference.

The present invention relates to the reduction of stress in ruminants in need thereof.

Methylsulfonylmethane (MSM, also known as dimethylsulfone), is a naturally occurring organosulfur compound and a putative methyl donor which is known to have several health benefits such as in particular normalizing the body functions in animals displaying symptoms of stress.

Methylsulfonylmethane naturally occurs in body fluids and tissues as well as in a variety of fresh foods including most fruits and vegetables, milk, and grains. Furthermore, it is marketed as a dietary supplement for humans and animals. Although present in a variety of foods, methylsulfonylmethane is readily lost due to its volatile nature. In addition, methylsulfonylmethane is not yet everywhere approved as feed additive. Thus, there is an ongoing need for ingredients which stimulate the endogenous production of methylsulfonylmethane in order to profit from its extraordinary health benefits.

Surprisingly it has now been found, that the supplementation of the methane inhibitors propanediol mononitrate respectively chloroform to ruminants leads to a significant increase in methylsulfonylmethane in the rumen fluid. Furthermore, animals in stress situations, when treated with propanediol mononitrate beforehand, show less symptoms of stress compared to respective control groups.

Thus, the present invention relates to a methane inhibitor respectively a composition comprising a methane inhibitor for the treatment or prophylaxis of the symptoms of stress in ruminants.

In a particular embodiment the invention relates to a method for the non-therapeutic alleviation or prophylaxis of the symptoms of stress in ruminants, said method including administering a methane inhibitor or a composition comprising a methane inhibitor to a ruminant prior to experiencing stress, while experiencing stress and/or after having experienced stress.

In another embodiment, the present invention relates to a method for enhancing the endurance to stress and/or lessening the symptoms of stress in ruminants, said method encompassing the step of administering an effective amount of a methane inhibitor to a ruminant in need thereof. Preferably, the methane inhibitor is administered in the form of a composition comprising the respective methane inhibitor, such as in the form of a premix, a feed composition or a feed additive.

In another embodiment, the invention relates to the use of a methane inhibitor for increasing endogeneous methyl donors such as in particular methylsulfonylmethane in the rumen fluid of a ruminant, in particular to enhance the endurance to stress and/or lessen the symptoms of stress.

The term methane inhibitor relates to all compounds suitable to reduce the methane emissions in ruminants (i.e. rumen methane inhibitors). Suitable methane inhibitors according to the present invention include garlic extracts, allicin, propanediol mononitrate, chloroform, nitrate, nitroethane, lauric acid, lauricidin as well as marine algae such as the Hawaiian micro-algae Chaetoceros without being limited thereto. Preferred methane inhibitors in all embodiments of the present invention are garlic extracts, allicin, chloroform and propanediol mononitrate. Most preferred in all embodiments of the present invention is the methane inhibitor propanediol mononitrate, which is particularly effective.

The term 'stress' as used herein is defined as the symptom resulting from exposure to a situation or environment that is not normal for an animal. Stress can often be seen when animals are handled and/or transported.

It is well understood by a person skilled in the art that the treatment of stress is non-therapeutically, e.g. to prevent or minimize deterioration of the well-being or health of a ruminant in periods of stress such as e.g. heat stress and/or stress due to transportation and/or slaughtering.

Advantageously, the methane inhibitor respectively the composition comprising the methane inhibitor is administered to the ruminant prior to the ruminant experiencing stress, while the ruminant is experiencing stress and/or after the ruminant experiences stress.

Thus, in a particular embodiment, the present invention relates to a method for the non-therapeutic alleviation or prophylaxis of the symptoms of stress in ruminants, said method including administering a methane inhibitor or a composition comprising a methane inhibitor to a ruminant prior to experiencing stress, while experiencing stress and/or after having experienced stress said method encompassing the consecutive steps of a.) assessing a present or future stress situation for a ruminant (in order to determine a ruminant in need of treatment) and b.) administering to the ruminant in need thereof an effective amount of the methane inhibitor.

In an advantageous embodiment, the present invention relates to the treatment (alleviation) of or prophylaxis against the symptoms of stress induced by temperature (heat), poor ventilation, overcrowding, transportation, slaughtering as well as pests, preferably induced by heat, transportation and/or slaughtering.

The symptoms of stress in ruminants include lethargy, decrease in or lack of appetite, an elevated or increased respiratory rate, signs of dehydration and/or an elevated heart rate.

Thus, in another embodiment the present invention relates to a methane inhibitor or a composition comprising the methane inhibitor as well as any methods and uses thereof according to the present invention for the treatment (alleviation) of or prophylaxis against lethargy, a decrease in or lack of appetite, an elevated or increased respiratory rate, dehydration and/or an elevated heart rate.

In one advantageous embodiment the present invention is directed to methods for feeding a methane inhibitor respectively a composition comprising a methane inhibitor to ruminants experiencing heat stress or that may become heat stressed, for example, due to high temperatures, humidity, dew points or combinations thereof.

In another advantageous embodiment, the present invention is directed to methods for preventing or minimizing deterioration of the well-being or health of a ruminant during heat stress, said method including determining a ruminant is experiencing heat stress or may become heat stressed followed by feeding said ruminant an effective amount of a methane inhibitor respectively a composition comprising a methane inhibitor.

Periods of heat stress can easily be determined by a person skilled in the art e.g. by observing two or more of an about 10 percent decrease in dry matter intake, reduced performance, increased respirations, elevated internal body temperature, open mouth breathing, increased panting, sweating, or failed reproduction. Alternatively or in addition the potential for heat stress can be easily be determined based on one or more of historical weather patterns or short-term weather forecasts.

In a further advantageous embodiment, the present invention relates to a method for preventing or minimizing deterioration of the well-being or health of a ruminant during transportation and/or slaughtering comprising the step of administering said ruminant with an effective amount of a methane inhibitor respectively a composition comprising a methane inhibitor for an effective period of time.

In the present context, a ruminant is a mammal of the order Artiodactyla that digests plant-based food by initially softening it within the animal's first stomach, known as the rumen, then regurgitating the semi-digested mass, now known as cud, and chewing it again. The process of again chewing the cud to further break down plant matter and stimulate digestion is called "ruminating".

Ruminants according to the present invention include cattle, goats, sheep, giraffes, American bison, European bison, yaks, water buffalo, deer, camels, alpacas, llamas, wildebeest, antelope, pronghorn, and nilgai.

Propanediol mononitrate (also referred to 1,3-propanediol mononitrate or PDMN [CAS-No: 100502-66-7]) is a known compound which can e.g. be manufactured as outlined in WO2004043898 or WO2012084629 and is available at DSM Nutritional Products Ltd.

The methane inhibitor, respectively the composition according to the present invention are preferably administered to the ruminant for an effective period of time sufficient to enhance the endurance to stress and/or lessen the symptoms of stress.

In all embodiments of the present invention the methane inhibitor such as in particular the propanediol mononitrate or chloroform can be administered as such or in the form of a composition comprising said methane inhibitor.

In any or all of the embodiments herein, the methane inhibitor respectively the composition comprising the methane inhibitor is preferably administered to the animal for an effective period of time to enhance the endurance to stress and/or lessen the symptoms of stress, particularly at set intervals. The set interval can be daily, or it can be more or less frequently than that. Preferably, the set interval is daily.

The effective period of time may be easily selected by a person skilled in the art based on the symptoms and the severity of the symptoms or the envisaged stress situation, which is to come and may be at least 1 day, at least 3 days, at least 7 days, at least 30 days, at least 60 days, or at least 90 days or a period of time lasting from 1 day to 200 days, from 1 day to 90 days, from 1 day to 60 days, from 1 day to 45 days, from 1 day to 30 days or from 3 days to 21 days.

In all embodiments of the present invention the effective period of time is preferably within a period of about 0.05 to about 72 hours, preferably about 1 to about 48 hours prior to the envisaged stress situation such as in particular heat stress and/or transportation from one location to another location; or within a period of about 0.05 to about 72 hours, preferably about 1 to about 48 hours after the stress situation such as in particular heat stress and/or transportation from one location to another location; or within a period of stress such as in particular during heat stress and/or during transportation from one location to another location.

The term 'an effective amount' as used herein refers to an amount necessary to obtain the desired reduction of the stress level. The physiological effect may be achieved by one single dose or by repeated doses. The effective amount of the methane inhibitor in the methods according to the invention may vary depending upon known factors, such as the physiological characteristics of the particular composition and its mode and route of administration; the age, health and weight of the ruminant; the nature and extent of the symptoms; the kind of concurrent treatment; the frequency of treatment; and the effect desired which can be determined by the expert in the field with normal trials, or with the usual considerations regarding the formulation.

In all embodiments of the present invention, the effective amount of the methane inhibitor to be administered to the ruminants is preferably selected in the range of 0.05 to 5 methane inhibitor/animal/day, more preferably in the range of 0.1 to 4 g methane inhibitor/animal/day, most preferably in the range of 0.5 to 3 g methane inhibitor/animal/day.

Advantageously, in all embodiments of the present invention, the methane inhibitor respectively the composition comprising the methane inhibitor is administered prophylactically, or when the animal has or is at a particular risk of developing stress such as preferably before transportation and/or slaughtering or if heat stress is to be foreseen e.g. in particular hot summers.

Thus, in one preferred embodiment the invention relates to a method of enhancing the endurance to stress in ruminants which is at risk of developing stress, preferably stress due to transportation and/or slaughtering, said method encompassing the administration of an effective amount of a methane inhibitor respectively a composition comprising the methane inhibitor to the ruminant at least 1 day before transportation and/or slaughtering, preferably at least 5 days, more preferably a least 10 days before transportation and/or slaughtering. Preferably, the methane inhibitor respectively a composition comprising the methane inhibitor is administered at least once a day starting 20 days prior to the risk of developing stress, preferably 10 days prior to the risk of developing stress, most preferably 5 days prior to the risk of developing stress. The method is in particular suitable for beef cattle and sheep.

In another preferred embodiment, the invention relates to a method of reducing the severity of heat stress in ruminants, said method encompassing the administration of an effective amount of a methane inhibitor respectively a composition comprising the methane inhibitor to a ruminant exposed to or to be exposed to heat stress. Heat stress may occur when a ruminant is exposed to a humidity index of 68 or greater, 75 or greater, or >79.

In all embodiments of the present invention, domestic cattle, sheep and goat are the more preferred species. For the present purposes, most preferred species are domestic cattle. The term includes all races of domestic cattle, and all production kinds of cattle, in particular dairy cows and beef cattle.

A particularly preferred group of ruminants in all embodiments according to the present invention are dairy cows, in particular lactating dairy cows or beef cattle.

Dairy cows may be administered the methane inhibitor respectively the composition comprising the methane inhibitor before lactation, during lactation or after lactation onset. If the composition is administered before lactation, this can be from 90 days prior to lactation onset to 1 day prior to lactation onset, preferably from 45 days prior to lactation onset to 10 days prior to lactation onset. The composition may be administered daily prior to lactation onset.

The methane inhibitor respectively the composition comprising the methane inhibitor may also be administered pre- or post-calving for a suitable number of days. For example, the composition may be administered to the animal for 40 days to 100 days post calving, or for 45 days to 95 days post calving, or for 50 days to 90 days post calving.

The composition according to the present invention may be formulated in any suitable form, including a powder, a granule, a pellet, a solution, or a suspension.

In one embodiment, the composition can be a dry, free-flowing powder (powderous formulation) suitable for direct inclusion into a commercially-available feed or as a supplement to a total mixed ration or diet. The powderous formulation may be mixed with either solid or liquid feed or with water. In another embodiment, the composition can be formed into pellets.

In all embodiments of the present invention, the composition comprising the methane inhibitor preferably is a powderous formulation comprising the methane inhibitor and a carrier material. Suitable carrier includes any carrier well known in the food and feed industry such as silicone dioxide without being limited thereto.

If the composition is a powderous formulation comprising the methane inhibitor and a carrier material, the methane inhibitor is usually sprayed onto or admixed with the carrier material by standard methods in the art, e.g. by using solvent suitable for the preparation of food or feed products such as e.g. dichloromethane followed by evaporation of the organic solvent.

Alternatively, the methane inhibitor can be diluted in a suitable edible oil before being sprayed onto or admixed with the carrier material. The powderous formulation may in addition contain usual additives used in the preparation of powderous formulations for feed application.

The amount of the methane inhibitor in the composition according to the present invention, in particular in a powderous formulation is preferably selected in the range of 1 to 20 wt.-%, preferably in the range of 2 to 15 wt.-%, most preferably in the range of 4 to 12 wt.-%, based on the total weight of the composition.

The methane inhibitor respectively the composition comprising the methane inhibitor according to the present invention such as in particular the powderous formulation is preferably administered admixed with the animal's feed, wherein the term feed refers to any compound, preparation, mixture, or composition suitable for, or intended for intake by an animal. Exemplary feed for ruminants such as cows include forage (grass, legumes, silage), hay, grass, grain as well as soy without being limited thereto.

When incorporated directly into the animal's feeds, the methane inhibitor respectively the composition comprising the methane inhibitor according to the present invention may be added in amounts ranging from 0.1 to 100 kg per ton, such as from 0.1 to 20 kg per ton (2000 pounds) of feed. In some embodiments, the composition can be added to animal feedstuffs in amounts from 0.1 kg to 50 kg per ton, from 0.1 to 20 kg per ton, or from 0.5 kg to 10 kg per ton of feed. In certain embodiments, the composition may be added to feeds in amounts ranging from 1 to 5 kg per ton of feed.

When expressed as a percentage of dry matter of feed, the methane inhibitor respectively the composition comprising the methane inhibitor may be added to animal feedstuffs in amounts ranging from 0.01 to 2.5% by weight, such as from 0.0125% to 2% by weight. In one embodiment, the composition can be added to animal feedstuffs in amounts from 0.05 to 1.5% by weight, such as from 0.06% to 1% by weight. In another embodiment, the composition can be added in amounts from 0.1 to 0.7% by weight, such as from 0.125% to 0.5% by weight of feed.

Alternatively, the methane inhibitor respectively the composition comprising the methane inhibitor such as in particular the powderous formulation according to the present invention may be fed directly to the animal as a supplement in amounts of from 0.01 gram to 20 gram per kilogram of live body weight per day, such as from 0.01 gram to 10 gram per kilogram, 0.01 gram to 5 gram, 0.01 gram to 1 gram, 0.015 gram to 1 gram, or 0.02 gram to 0.4 gram per kilogram of live body weight per day.

One of skill in the art can appreciate that the amount of the methane inhibitor respectively the composition comprising the methane inhibitor fed can vary depending upon the amount of methane inhibitor incorporated in the composition, the animal species, the size of the animal and the type of the feedstuff to which the claimed methane inhibitor respectively the composition comprising the methane inhibitor is added.

In a particular advantageous embodiment, the methane inhibitor respectively the composition comprising the methane inhibitor is used for treating animals that already suffer from stress induced by their environment, heat, nutrition, and/or transportation, in particular by heat and transportation.

Preferably, in all embodiments of the present invention the endogenous methylsulfonylmethane in the rumen fluid is increased by at least 100%, preferably by at least 200%, more preferably by at least 300% based on the control by the administration of the methane inhibitor respectively the composition comprising the methane inhibitor.

The present invention is further described by the following examples which should not be construed as limiting the scope of the invention.

EXPERIMENTAL PART

Eight fistulated Brahman steers (*Bos indicus*) were randomly allocated to two groups (4 animals per group) and received a forage ad libitum diet (Rhode grass hay (*Chloris gayana*), chemical composition: DM, 917 g/kg fresh matter; in g/kg of DM: OM, 806; CP, 169; NDF, 661; ADF, 359; ADL, 46; ash, 116 and GE 17.38 MJ/kg). The treatments used were chloroform fixed in cyclodextrin (reference) and propanediol mononitrate (10% purity on silicon dioxide). Animals were adapted to the diet over a 21 d period. After that initial period, experimental animals were placed into individual pens in an animal house for the measurement of intakes (10 d) and were treated with cyclodextrin (2 g/100 kg LW) and molasses (60 mL/d). On the last 2 days animals were placed into open-circuit respiration chambers for collection of rumen samples. Following the initial adaption/control period one group of animals received the chloroform+60 mL of molasses during 21 days (1.6 g choloroform–CD/100 kg LW) and the second group received the propanediol mononitrate treatment during 21 days (2.5 g propanediol mononitrate/animal/day). propanediol mononitrate was provided to the animals mixed with molasses (60 mL/day, molasses were previously diluted in water: 1:4 water:molasses) and mixed with the hay at three different times: 0 h, 3 h and 5 h after the feed was offered. propanediol mononitrate group was treated with comparative amounts of cyclodextrin as the chloroform group during the experiment. On days 20 and 21 of treatment both groups were placed in open-circuit respiration chambers for rumen fluid collection.

Rumen fluid samples (approx. 60 mL per animal) were collected using a probe with 2 layers of cheesecloth through the cannula of the animal at 3 h post feeding, during confinement in respiration chambers to determine rumen metabolites. The metabolites were quantified using Nuclear Magnetic Resonance spectroscopy in the NMR facilities of the Institute for Molecular Bioscience and of the Queensland NMR Network (QNN) at the University of Queensland in

TABLE 1

Effects of PDMN on rumen metabolites compared with control period (μmol/L rumen fluid).

| Metabolite | Control | PDMN | SEM[a] | P-value |
|---|---|---|---|---|
| Dimethylsulfone | 20 | 113 | 3.84 | 0.001 |

[a]SEM, standard error of the mean

TABLE 2

Effects of chloroform on rumen metabolites compared with control period (μmol/L rumen fluid)

| | Control | Chloroform | SEM[a] | P-value |
|---|---|---|---|---|
| Dimethylsulfone | 21 | 80 | 3.85 | 0.007 |

[a]SEM, standard error of the mean

As can be retrieved, the treatment with the methane inhibitors propanediol mononitrate and chloroform lead to a statistically significant increase of the methyl donor, while propanediol mononitrate is particularly effective.

The invention claimed is:

1. A non-therapeutic method for alleviating or reducing stress symptoms of a ruminant, the method comprising administering to the ruminant in need of alleviation or reduction of stress symptoms an effective amount of propanediol mononitrate or chloroform to increase endogeneous methyl donors in rumen fluid of the ruminant prior to experiencing stress, while experiencing stress and/or after having experienced stress.

2. The method according to claim 1, wherein the propanediol mononitrate or chloroform is administered at least 1 day prior to the ruminant experiencing stress.

3. The method according to claim 1, wherein the propanediol mononitrate or chloroform is administered at least 5 days prior to the ruminant experiencing stress.

4. The method according to claim 1, wherein the propanediol mononitrate or chloroform is administered at least 10 days prior to the ruminant experiencing stress.

5. The method according to claim 1, wherein the amount of the propanediol mononitrate or chloroform is sufficient to increase methylsulfonylmethane in rumen fluid of the ruminant.

6. The method according to claim 1, wherein the propanediol mononitrate or chloroform is administered in the form of a powderous formulation comprising the propanediol mononitrate or chloroform and a carrier material.

7. The method according to claim 6, wherein the carrier material is silicone dioxide.

8. The method according to claim 1, wherein the ruminant is selected from the group consisting of domestic cattle, sheep and goats.

9. The method according to claim 8, wherein the domestic cattle is selected from the group consisting of dairy cows and beef cattle.

10. The method according to claim 1, wherein the propanediol mononitrate or chloroform is administered to beef cattle before transportation and/or slaughtering.

11. The method according to claim 10, wherein the propanediol mononitrate or chloroform is administered to the beef cattle at least 1 day prior to the transportation and/or slaughtering of the beef cattle.

12. The method according to claim 10, wherein the propanediol mononitrate or chloroform is administered to the beef cattle at least 5 days prior to the transportation and/or slaughtering of the beef cattle.

13. The method according to claim 10, wherein the propanediol mononitrate or chloroform is administered to the beef cattle at least 10 days prior to the transportation and/or slaughtering of the beef cattle.

* * * * *